United States Patent
Li et al.

(10) Patent No.: US 8,088,122 B2
(45) Date of Patent: Jan. 3, 2012

(54) OPTICAL EAR INFECTION TREATMENT DEVICE AND METHOD

(75) Inventors: Kasey Kai-Chi Li, Palo Alto, CA (US); George Yoseung Choi, Redwood City, CA (US); Luiz B. Da Silva, Danville, CA (US)

(73) Assignee: George Y. Choi, Menlo Park, CA (US)

( * ) Notice: Subject to any disclaimer, the term of this patent is extended or adjusted under 35 U.S.C. 154(b) by 0 days.

(21) Appl. No.: 11/828,236

(22) Filed: Jul. 25, 2007

(65) Prior Publication Data
US 2008/0097414 A1    Apr. 24, 2008

Related U.S. Application Data

(60) Provisional application No. 60/838,545, filed on Aug. 17, 2006.

(51) Int. Cl.
*A61B 18/18*    (2006.01)

(52) U.S. Cl. .................. 606/3; 606/10; 606/13; 606/15; 607/88; 607/92

(58) Field of Classification Search .......... 606/3, 10–16; 607/88–93, 137
See application file for complete search history.

(56) References Cited

U.S. PATENT DOCUMENTS

| | | | | |
|---|---|---|---|---|
| 4,712,537 A | * | 12/1987 | Pender | 600/200 |
| 5,591,157 A | * | 1/1997 | Hennings et al. | 606/3 |
| 5,830,211 A | * | 11/1998 | Santana et al. | 606/27 |
| 6,389,313 B1 | * | 5/2002 | Marchitto et al. | 604/21 |
| 7,167,622 B2 | * | 1/2007 | Temelkuran et al. | 385/123 |
| 7,226,470 B2 | * | 6/2007 | Kemeny et al. | 607/94 |
| 7,559,945 B2 | * | 7/2009 | Breden et al. | 607/88 |
| 7,704,259 B2 | * | 4/2010 | Kaplan et al. | 606/109 |

OTHER PUBLICATIONS

Arakane, K. et al, "Singlet oxygen (1 delta g) generation from coproporphyrin in Propionibacterium acnes on irradiation," *Biochem Biophys Res Commun*, vol. 223, pp. 578-582, 1996.
Futsaether, CM, et al, "Intracellular pH changes induced in Propionibacterium acnes by UVA radiation and blue light," *J Photochem Photobiol B*, vol. 31, pp. 125- 131, 1995.
PCT International Patent Application No. PCT/US2007/074503 filed Jul. 26, 2007 in the name of Choi et al., International Preliminary Report on Patentability mailed Feb. 26, 2009.
PCT International Patent Application No. PCT/US2007/074503 filed Jul. 26, 2007 in the name of Choi et al., International Search Report and Written Opinion mailed Sep. 18, 2008.
Taylor, Barry L. et al, "Electron Acceptor Taxis and Blue Light Effect on Bacterial Chemotaxis," *Journal of Bacteriology*, vol. 40:2, pp. 567-573, Nov. 1979.

* cited by examiner

*Primary Examiner* — Ahmed Farah
(74) *Attorney, Agent, or Firm* — Levine Bagade Han LLP

(57) ABSTRACT

Optical ear infection treatment device and methods are described where an LED and optical light pipe are used to deliver the light from the LED to the middle ear of a patient to reduce bacterial growth and/or eliminate bacteria. Typically, the device is placed in the ear and then activated by the user by pressing an activation button. Once activated the control electronics will turn on the LED and perform a treatment. The most basic treatment mode comprises turning on the LED at maximum power for a predetermined period, e.g. 30 minutes, 60 minutes. When the preset duration is completed, the device will notify the user by an audible beep or vibration that the treatment is complete. Once completed the user can remove the device, the treatment could be repeated once a day or for extreme cases multiple times during the day.

26 Claims, 3 Drawing Sheets

OPTICAL EAR INFECTION TREATMENT DEVICE AND METHOD

CROSS-REFERENCE TO RELATED APPLICATIONS

This application claims the benefit of priority to U.S. Prov. Pat. App. 60/838,545 filed Aug. 17, 2006, which is incorporated herein by reference in its entirety.

BACKGROUND OF THE INVENTION

In the United States, three out of four children experience an ear infection before they are three years old. Each year more than 7 million people require medication or treatment for ear infections. In most cases these bacterial infections are treated with antibiotics. The broad use of antibiotics has led to drug resistant strains of bacteria that are difficult to eliminate. Moreover, many patients acquire chronic infections and chronic ear diseases, requiring multiple surgical interventions including the placement of ventilation tubes, adenotonsillectomy and mastoidectomy.

A need exists for an alternative approach to treating ear infections that is safe, non-invasive, and which potentially reduces or eliminates the need for antibiotic therapy. The present invention fulfills this need and further provides related advantages.

BRIEF SUMMARY OF THE INVENTION

It is an object of the present invention to provide a device and method for treating ear infections. These and other objects will be apparent to those skilled in the art based on the teachings herein.

One embodiment is a device comprising a battery, control electronics, Light Emitting Diode (LED) and optical light pipe to deliver the light from the LED to the middle ear where it can reduce bacterial growth and/or eliminate bacteria. In normal use the device is placed in the ear and then activated by the user by pressing an activation button. Once activated the control electronics will turn on the LED and perform a treatment. The most basic treatment mode consists of turning on the LED at maximum power for a predetermined period (e.g. 30 minutes, 60 minutes) that has been shown to be bacterial static or bacterial cidal. When the preset duration is completed, the device will notify the user by an audible beep or vibration that the treatment is complete. Once completed the user can remove the device, the treatment could be repeated once a day or for extreme cases multiple times during the day. Alternative modes of treatment would turn ON the LED multiple times for a shorter period of time (e.g. 5 minutes, 10 minutes, 15 minutes) followed by a time period (e.g. 10 minute, 30 minute, 60 minute, 120 minute) with the LED OFF. This ON and OFF cycle could be repeated continuously for a day or multiple days. The total amount of light used in any one treatment period allows all surfaces of the middle ear to receive a total light fluence of 0.1 $J/cm^2$ to 500 $J/cm^2$ which is adequate to effectively kill bacteria. The wavelength of the LED is in the range of 400 nm to 700 nm with the most effective wavelength range being 400 nm to 500 nm.

In another embodiment, the light source used is a high intensity flash or laser source that can provide a high amount of optical energy in a short duration.

Another aspect is methods of use of the device in the killing of bacteria in the middle ear and Eustachian tube.

Other objects and advantages of the present invention will become apparent from the following description and accompanying drawings.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

All publications and patent applications mentioned in this specification are herein incorporated by reference to the same extent as if each individual publication or patent application was specifically and individually indicated to be incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention, and that methods and structures within the scope of these claims and their equivalents be covered thereby.

The present invention is a device comprising a battery, control electronics, Light Emitting Diode (LED) and optical light pipe to deliver the light from the LED to the middle ear where it can kill bacteria. In one embodiment, the present invention the light is in the UV-Blue wavelength range (240-490 nm) and bacteria is killed through photodynamic production of oxygen radicals (Arakane K, Ryu A, Hayashi C et al. *Singlet oxygen (1 delta g)generation from coproporphyrin in Propionibacterium acnes on irradiation*. Biochem Biophys Res Commun 1996; 223: 578-82; Barry L. Taylor, et al. *Electron Acceptor Taxis and Blue Light Effect on Bacterial Chemotaxis*, JOURNAL OF BACTERIOLOGY, November 1979, p. 567-573). It has also been shown that UVA and blue light can induce intracellular pH changes that can damage and ultimately kill bacteria (Futsaether C M, Kjeldstad B, Johnsson A. *Intracellular pH changes induced in Propionibacterium acnes by UVA radiation and blue light*. J Photochem Photobiol B 1995; 31: 125-31). When the control electronics determines the length of time for treatment depending on the optical power needed to effectively kill the bacteria. In most cases the total optical flux is less than 500 $J/cm^2$ and for most applications less than 100 $J/cm^2$.

Device

Figure 1:
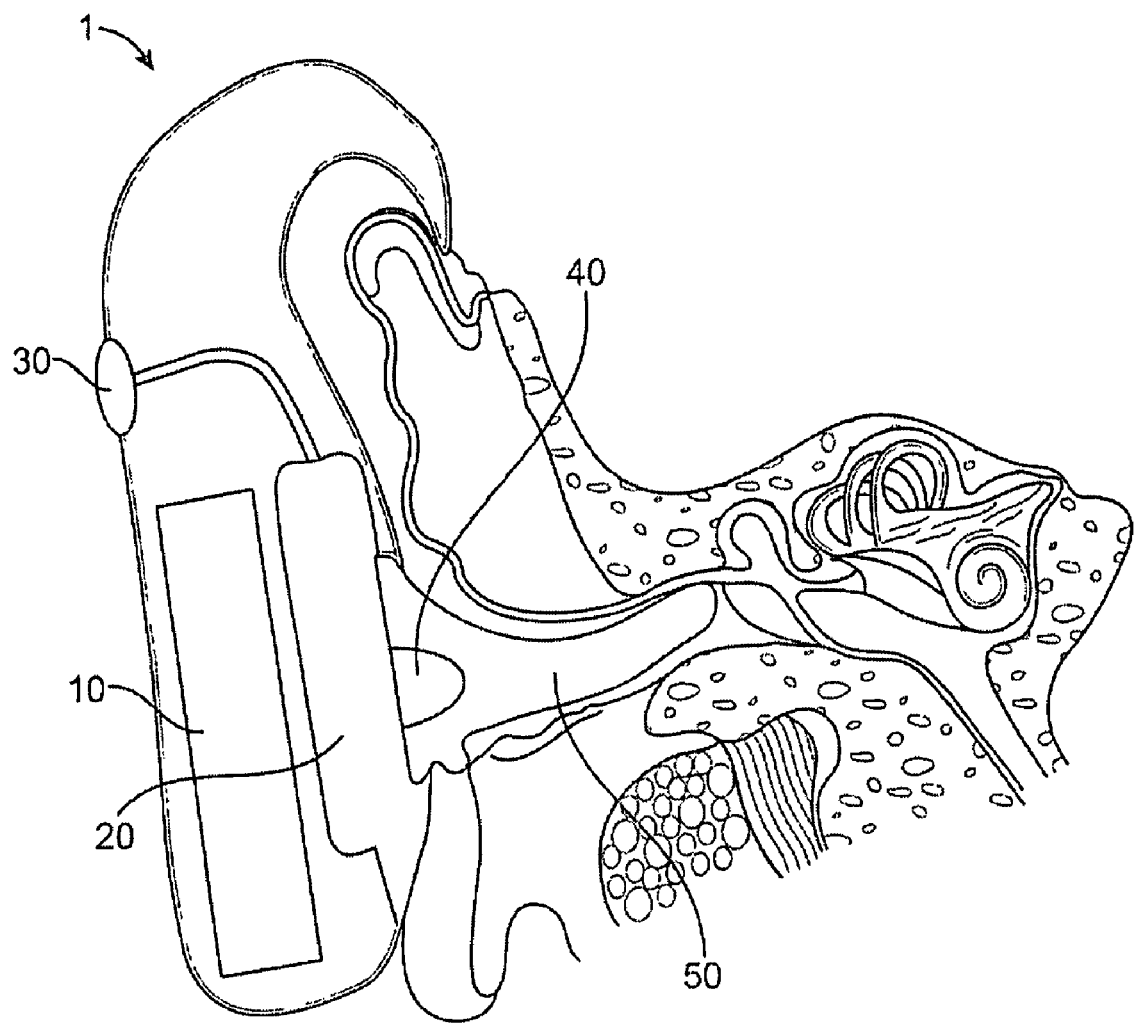
FIG. 1 shows a sectional view of the present invention and how it would be used to treat an ear infection.

FIG. 1 shows a cross section of the device 1 and ear showing how it would be used to treat a middle ear infection. The main components of the device 1 include a battery 10, control electronics 20, an activation button 30, and a light emitting diode (LED) 40 integrated within a housing, and an optical light pipe 50 extending from the housing and in optical communication with the LED 40. When activated by the user by pressing button 30, the control electronics 20 power the LED 40 and light couples from the LED 40 into the light pipe 50 that transports the light into the middle ear. The device 1 is compact and can easily be clipped behind the ear as shown. When a treatment is started the control electronics turn on the LED 40 for a period typically 20 to 60 minutes (although treatment may be effected for fewer than 20 minutes or greater than 60 minutes) to effectively illuminate the inner ear and kill bacteria. When the treatment cycle is complete the control electronics sound a tone to indicate to the user that the device can be removed. In an alternative embodiment a vibration is generated by the control electronics to alert the user that the device can be removed. The center wavelength of the LED is typically in the range of 400 nm-500 nm, and for best efficacy in the range 420 nm-470 nm, in one embodiment longer wavelength LED's (500 nm-700 nm) which have a higher penetration depth through tissue and fluid are used to kill bacteria. At these longer wavelengths the mechanism can be thermal or through photodynamic production of oxygen radicals.

In one embodiment, the optical light pipe 50 is made of flexible and optically transparent polymers. The central core of the light pipe has a higher index of refraction then a surrounding thin cladding (<100 micron) which helps guide the light down the light pipe and direct it through the eardrum. Using soft polymers or plastics (e.g. silicone) reduces the risk of damaging or irritating the ear canal. Since the total propagation path is typically less than 5 cm, plastics with some absorption or scattering are acceptable. In addition the outer wall of the optical light pipe 50 can be coated with a thin metal coating to prevent light from radiating out the side of the light pipe 50. In order to prevent any skin reaction the light pipe can have a thin outer coating of biocompatible polymer for example TEFLON (E.I. Du Pont De Nemours, Wilmington, Del.) or polyetheretherketones (PEEK). Since the device is intended for short term use it is not necessary to use materials that are suitable for permanent implant.

In alternative embodiment, the optical light pipe 50 is formed from a flexible hollow tube that has the inner wall coated with a reflective coating (e.g. aluminum, gold) to guide the light down the tube and direct it at the eardrum.

In an alternative embodiment the single activation button 30 is replaced by a series of buttons to allow the user to control treatment mode and operating features of the device including whether the device uses sound or vibration to indicate the end of treatment.

In an alternative embodiment the tip of the light pipe 50, is tapered to puncture the ear drum and deliver more light directly into the Eustachian tube. This maybe utilized in cases where thick layers of fluids and bacteria have filled the Eustachian tube and middle ear preventing light for effectively transmit through the eardrum.

In an alternative embodiment the battery, control electronics and LED are in a separate device that can be put into a pocket, or attached to the waist. A flexible fiber optic cable connects the device to a small earplug that contains the optical light pipe. This embodiment allows for larger batteries and larger LEDs that are impractical for a compact device that attaches to the ear.

Figure 2:
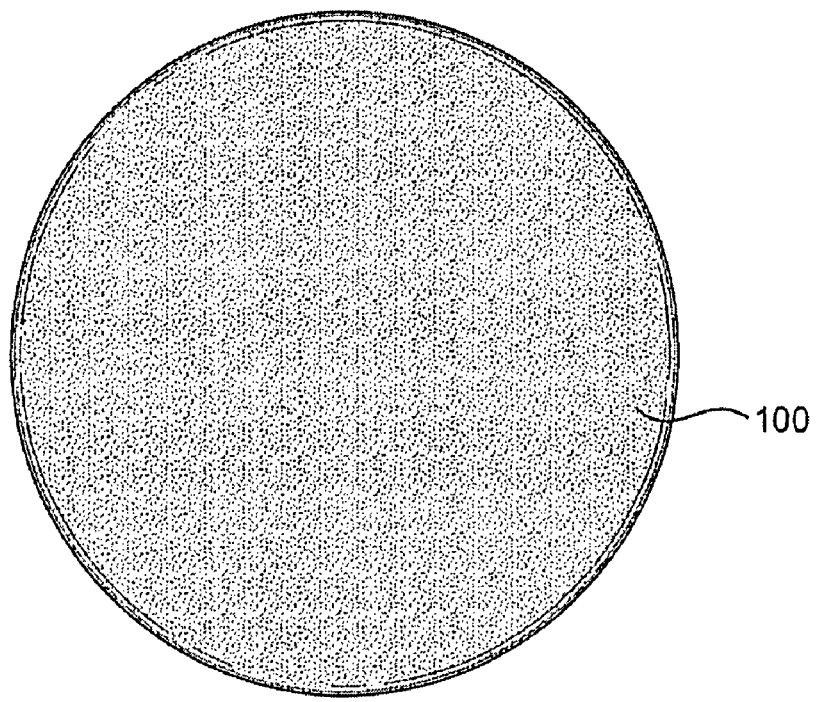
FIG. 2 compares the growth of pseudomonada bacteria on a control Petri dish compared to a Petri dish where light has illuminated the center.
Figure 2:
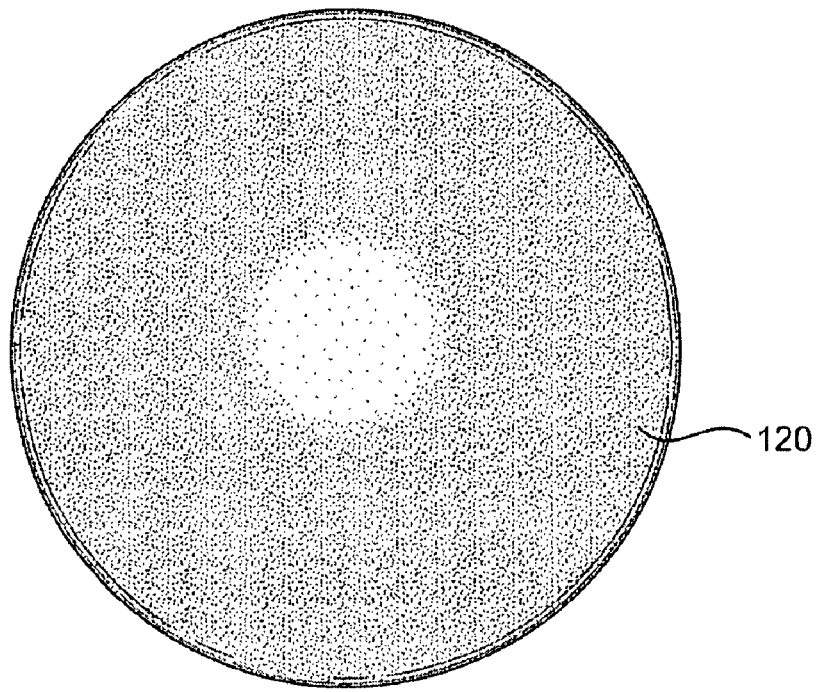
Figure 3:
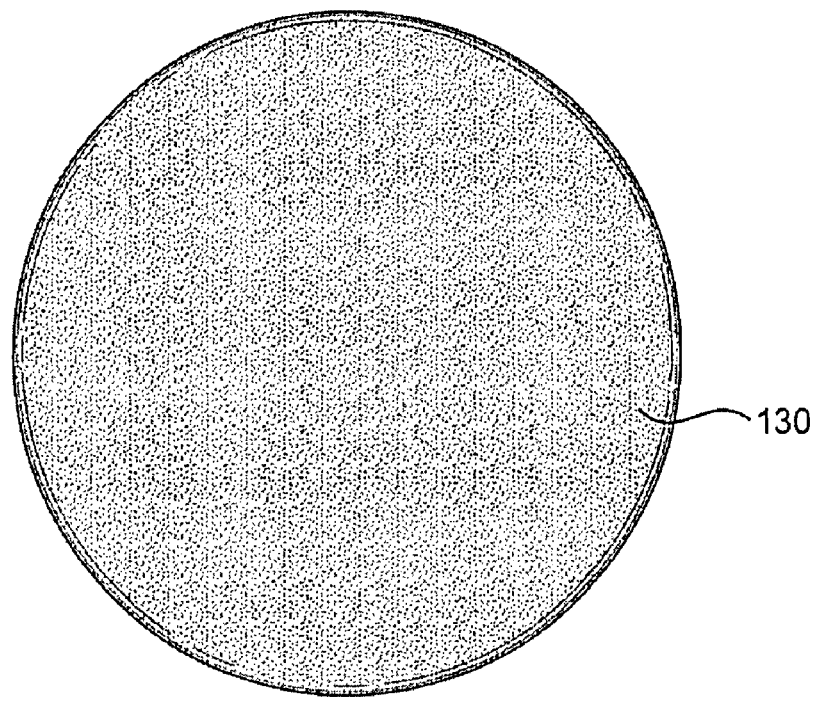
FIG. 3 compares the growth of *staphylococcus aureus* bacteria on a control Petri dish compared to a Petri dish where light has illuminated the center.
Figure 3:
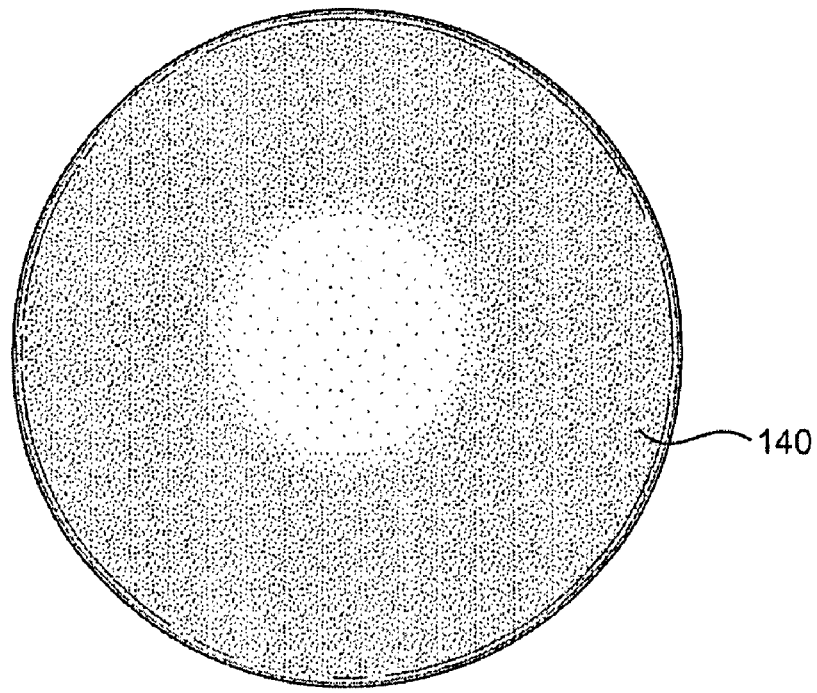

FIG. 2 shows how LED illumination was used to kill bacteria growing on a culture. Each Petri dish consisted of a growth medium with a thin growing layer of pseudomonada bacteria. The control Petri dish 100 was not illuminated and shows uniform bacterial growth. Petri dish 120 was illuminated in the center with an LED having a center wavelength of 420 nm for 20 minutes. The illuminated Petri dish shows a clear region in the center with no bacteria corresponding to the area illuminated with LED light. The total optical fluence in the 20 minute procedure was approximately 250 J/cm$^2$. FIG. 3 shows similar results for *staphylococcus aureus* bacteria where the Petri dish 130 is the control which was not illuminated and which shows uniform bacterial growth and Petri dish 140 shows a clear region in the center with no bacteria corresponding to the area illuminated with LED light. Petri dish 140 was illuminated similarly for 20 minutes in its center at approximately 250 J/cm$^2$.

METHOD OF USE

The devices described herein are suitable for use in the treatment and control of bacteria or fungal infections in the inner ear.

Once a day or if necessary multiple times during the day the device is inserted into the ear canal and activated for treatment. The control electronics 20 may turn on the LED 40 and monitor the radiated optical power. When the necessary total optical power has been radiated the LED 40 may be turned off automatically or manually. An audible sound or vibration is produced to notify the user that the treatment is complete at which time the user removes the device from the ear.

The above descriptions and illustrations are only by way of example and are not to be taken as limiting the invention in any manner. One skilled in the art can substitute known equivalents for the structures and means described. The full scope and definition of the invention, therefore, is set forth in the following claims.

What is claimed is:

1. A device for treating an ear infection in a user, comprising:
    a light emitting diode;
    a light pipe sized for placement directly within an ear canal and configured to transport light emitted from the light emitting diode to a middle ear region along a propagation path of less than 5 cm;
    a control in electrical communication with the light emitting diode, wherein the control is operable by the user; and
    an indicator for notifying the user of completion of a treatment.

2. The device of claim 1 wherein the light emitting diode is configured to emit light at a wavelength of 400 nm to 700 nm.

3. The device of claim 2 wherein the light emitting diode is configured to emit light at a wavelength of 400 nm to 500 nm.

4. The device of claim 2 wherein the light emitting diode is configured to emit light at a wavelength of 420 nm to 470 nm.

5. The device of claim 2 wherein the light emitting diode is configured to emit light at a wavelength of 500 nm to 700 nm.

6. The device of claim 1 wherein the device comprises a housing configured to attach to an ear of the user.

7. The device of claim 1 wherein the light pipe is comprised of a flexible and optically transparent polymer.

8. The device of claim 7 wherein the polymer comprises silicone.

9. The device of claim 7 wherein the light pipe comprises a central core having an index of refraction which is higher relative to an index of refraction of a cladding surrounding the central core.

10. The device of claim 9 wherein the cladding has a thickness of less than 100 microns.

11. The device of claim 1 wherein the light pipe further comprises a reflective coating to guide light from the light emitting diode through the light pipe.

12. The device of claim 11 wherein the reflective coating is comprised of aluminum or gold.

13. The device of claim 1 wherein the light pipe further comprises a biocompatible polymer coating.

14. The device of claim 1 wherein the light pipe defines a tapered tip configured to puncture through an ear drum of the user.

15. The device of claim 1 wherein the control comprises an actuator for manipulation by the user.

16. The device of claim 1 wherein the indicator is configured to vibrate to notify the user of completion of the treatment.

17. The device of claim 1 wherein the indicator is configured to emit an audible signal to notify the user of completion of the treatment.

18. The device of claim 1 wherein the control is configured to emit light from the light emitting diode for 20 minutes.

19. The device of claim 1 wherein the control is configured to emit light from the light emitting diode at an intensity of 250 J/cm$^2$.

20. The device of claim 1 further comprising a power supply in electrical communication with the light emitting diode.

21. A device for treating an ear infection, comprising:
a light emitting diode;
a light pipe configured to transport light emitted from the light emitting diode along a propagation path of less than 5 cm to a middle ear region;
a control in electrical communication with the light emitting diode; and
an indicator for notifying a user of completion of a treatment.

22. The device of claim 21 wherein the light emitting diode is configured to emit light at a wavelength of 400 nm to 700 nm.

23. The device of claim 22 wherein the light emitting diode is configured to emit light at a wavelength of 400 nm to 500 nm.

24. The device of claim 22 wherein the light emitting diode is configured to emit light at a wavelength of 420 nm to 470 nm.

25. The device of claim 22 wherein the light emitting diode is configured to emit light at a wavelength of 500 nm to 700 nm.

26. The device of claim 21 wherein the device comprises a housing configured to attach to an ear of the user.

\* \* \* \* \*